US009199291B2

(12) United States Patent
Hasegawa et al.

(10) Patent No.: US 9,199,291 B2
(45) Date of Patent: Dec. 1, 2015

(54) OPERATION MANAGEMENT DEVICE, OPERATION MANAGEMENT METHOD, AND OPERATION MANAGEMENT PROGRAM FOR HIGH-FREQUENCY RESISTANCE WELDING AND INDUCTION WELDING

(75) Inventors: Noboru Hasegawa, Tokyo (JP); Hideki Hamatani, Tokyo (JP); Takao Miura, Tokyo (JP); Kunihiko Hatabara, Tokyo (JP); Nobuo Mizuhashi, Tokyo (JP); Kazuto Yamamoto, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 497 days.

(21) Appl. No.: 13/581,488

(22) PCT Filed: Mar. 22, 2011

(86) PCT No.: PCT/JP2011/056748
§ 371 (c)(1),
(2), (4) Date: Aug. 28, 2012

(87) PCT Pub. No.: WO2011/118560
PCT Pub. Date: Sep. 29, 2011

(65) Prior Publication Data
US 2012/0325805 A1    Dec. 27, 2012

(30) Foreign Application Priority Data

Mar. 23, 2010    (JP) ................................. 2010-066357

(51) Int. Cl.
*B23K 13/01*    (2006.01)
*B23K 9/073*    (2006.01)
(Continued)

(52) U.S. Cl.
CPC .................. *B21C 51/00* (2013.01); *B21C 37/08* (2013.01); *B21C 37/0822* (2013.01); *B23K 11/0873* (2013.01); *B23K 13/046* (2013.01); *G01N 21/952* (2013.01); *G01N 2021/8411* (2013.01)

(58) Field of Classification Search
CPC .... B21C 37/08; B21C 37/0822; B21C 51/00; B23K 11/0873; B23K 13/046; G01N 21/952; G01N 2021/8411
USPC ............... 219/600–677, 69.1, 773, 465.1, 50, 219/59.1–67, 78.01–120, 121.11–162, 219/200–220, 482–553; 29/890.038, 29/890.039, 890.053, 33 D; 138/171, 170; 228/141.1, 144, 146, 147; 356/600–608; 318/567–568.25; 148/516–521
See application file for complete search history.

(56) References Cited

U.S. PATENT DOCUMENTS 1,998,139 A * 4/1935 Morgan ........................ 219/61.3
2,687,465 A * 8/1954 Crawford ...................... 219/612
(Continued)

FOREIGN PATENT DOCUMENTS

JP    61-126980    6/1986
JP    02-263581    10/1990
(Continued)

OTHER PUBLICATIONS

International Search Report dated Jun. 14, 2011, issued in corresponding PCT Application No. PCT/JP2011/056748.
(Continued)

*Primary Examiner* — Dana Ross
*Assistant Examiner* — Gyounghyun Bae
(74) *Attorney, Agent, or Firm* — Kenyon & Kenyon LLP

(57) ABSTRACT

An operation management device performs an operation management for electric resistance welding in which a strip-shaped metal plate is formed to have a cylindrical shape in such a manner that both end portions of the metal plate gradually face each other while the metal plate is conveyed, and a Vee convergence section, which is a portion at which both of the end portions butt against each other while facing each other, is welded. Furthermore, the operation management device includes: a measuring unit that measures a distance L [mm] between a first Vee convergence point at which both of the end portions of the metal plate geometrically come into contact with each other and a second Vee convergence point that is a contact point of both of the end portions of the metal plate, and a Vee convergence angle θ[°] at the first Vee convergence point on the basis of an image of an area including the Vee convergence section; and a determining unit that determines whether or not the distance L [mm] and the Vee convergence angle θ[°] satisfy the following equation (1).

$$L_{min}(\theta/\theta_{st})^{-0.15} \le L \le 35 \qquad (1)$$

2 Claims, 8 Drawing Sheets

(51) Int. Cl.
  *B23K 11/00*   (2006.01)
  *B23K 9/02*    (2006.01)
  *B21C 51/00*   (2006.01)
  *B21C 37/08*   (2006.01)
  *B23K 13/04*   (2006.01)
  *B23K 11/087*  (2006.01)
  *G01N 21/952*  (2006.01)
  *G01N 21/84*   (2006.01)

(56) References Cited

U.S. PATENT DOCUMENTS

| | | | | |
|---|---|---|---|---|
| 2,800,561 | A | * | 7/1957 | Shenk .............................. 219/612 |
| 2,817,364 | A | * | 12/1957 | Crawford ........................ 138/171 |
| 3,127,674 | A | * | 4/1964 | Kohler ............................ 228/147 |
| 3,619,535 | A | * | 11/1971 | Sullivan .......................... 219/612 |
| 3,619,542 | A | * | 11/1971 | Oppenheimer ................. 219/67 |
| 3,689,725 | A | * | 9/1972 | Hammer et al. ............... 219/613 |
| 4,314,125 | A | * | 2/1982 | Nakamura ..................... 219/609 |
| 4,354,090 | A | * | 10/1982 | Nilsen ....................... 219/121.63 |
| 4,443,677 | A | * | 4/1984 | DeSaw ........................... 219/613 |
| 4,596,913 | A | * | 6/1986 | Takechi et al. ................. 219/613 |
| 4,608,471 | A | * | 8/1986 | Vollmuth et al. .............. 219/613 |
| 4,649,256 | A | * | 3/1987 | Minamida et al. ........ 219/121.64 |
| 4,796,798 | A | * | 1/1989 | Tsuta et al. ..................... 228/146 |
| 4,965,499 | A | * | 10/1990 | Taft et al. ................... 318/568.11 |
| 5,245,409 | A | * | 9/1993 | Tobar ............................. 356/606 |
| 5,886,313 | A | * | 3/1999 | Krause et al. ............... 219/121.6 |
| 5,900,079 | A | * | 5/1999 | Ono et al. ....................... 148/519 |
| 2007/0095878 | A1 | * | 5/2007 | Scott et al. ..................... 228/102 |

FOREIGN PATENT DOCUMENTS

| | | |
|---|---|---|
| JP | 07-040061 | 2/1995 |
| JP | 2008-212961 | 9/2008 |
| JP | 2009-233578 | 10/2009 |
| JP | 2009-255132 | 11/2009 |

OTHER PUBLICATIONS

Lap and butt seam welding, a technical material of Japan Welding Soc. No. 10 (Nov. 1989), Department of Joining and Material Processing for Light Structures in Japan Welding Society, with a partial translation thereof.

* cited by examiner

OBSERVED PLATE EDGE PORTION

OBSERVED PLATE EDGE PORTION

| WELD STATE | 0mm | 0.3mm | 0.6mm | 0.9mm | OVERALL EVALUATION |
|---|---|---|---|---|---|
| A | NO GOOD | NO GOOD | NO GOOD | NO GOOD | NO GOOD |
| B | GOOD | GOOD | NO GOOD | NO GOOD | NO GOOD |
| C | GOOD | GOOD | GOOD | GOOD | GOOD |
| D | NO GOOD | NO GOOD | NO GOOD | NO GOOD | NO GOOD |

OPERATION MANAGEMENT DEVICE, OPERATION MANAGEMENT METHOD, AND OPERATION MANAGEMENT PROGRAM FOR HIGH-FREQUENCY RESISTANCE WELDING AND INDUCTION WELDING

FIELD OF THE INVENTION

The present invention relates to an operation management device, an operation management method, and an operation management program, which manage high frequency resistance welding or induction welding (hereinafter, referred to as electric resistance welding) in which a metal plate is continuously formed to have a cylindrical shape by a roller group while being conveyed, and both end portions of the metal plate, which are converged while forming a V-shape, are heated and butt against each other.

This application is a national stage application of International Application No. PCT/JP2011/056748, filed Mar. 22, 2011, which claims priority to Japanese Patent Application No. 2010-66357, filed Mar. 23, 2010, the content of which is incorporated herein by reference.

DESCRIPTION OF RELATED ART

Electric resistance welded steel pipes are used in a wide range of fields such as a line pipe for petroleum or natural gas, an oil well pipe, and a pipe for atomic power, terrestrial heat, a chemical plant, a mechanical structure, and general piping. In a facility of manufacturing the electric resistance welded steel pipe, a steel strip (strip-shaped steel plate) is continuously formed to have a cylindrical shape by a roller group in such a manner that both end portions (both end portions in a circumferential direction, both edges) of the steel strip gradually face each other while the steel strip is conveyed, and a Vee convergence section that is a portion at which both of the end portions butt against each other while facing each other is melted by heating and is welded. In the electric resistance welding, it is necessary to prevent insufficient heat input and excessive heat input by controlling the amount of heat input within an appropriate range.

As this kind of technology, Patent Citation 1 discloses a method of manufacturing an electric resistance welded steel pipe in which when a weld point at the time of non-welding is set as an origin on the basis of image data obtained by imaging a contact point including weld metal and the periphery thereof under a condition that the plate thickness t (mm) of the steel plate and an angle of the edge surfaces φ satisfy the following equation (101), the amount of heat input is controlled in such a manner that a position of a weld point is −2.0 mm or less in a welding direction.

$$0 \leq \phi \leq \tan(0.4/t)^{-1} \quad (101)$$

In addition, Patent Citation 2 discloses a method of manufacturing an electric resistance welded steel pipe in which areas in the vicinity of a weld point of a workpiece are continuously imaged by a high-speed camera, a length of a narrow gap section from the weld point to a Vee convergence position is measured on the basis of the image, and welding heat input in the electric resistance welding is adjusted in such a manner that the measured length L of the narrow gap section satisfies the following equation (102).

$$0.259t+0.013d-0.00548v-6.16 < L < 0.259t+0.013d-0.00548v+23.84 \quad (102)$$

t: Plate thickness (mm) of a metallic strip, d: Outer diameter (mm) of a pipe, v: Welding speed (mm/s)

PATENT CITATION

[Patent Citation 1] Japanese Unexamined Patent Application, First Publication No. 2008-212961
[Patent Citation 2] Japanese Unexamined Patent Application, First Publication No. 2009-233678

NON PATENT CITATION

[Non Patent Citation 1] Lap and butt seam welding, a technical material of Japan Welding Soc. No. 10 (November 1989), Department of Joining and Material Processing for Light Structures in Japan Welding Society

SUMMARY OF THE INVENTION

Problems to be Solved by the Invention

However, the method disclosed in Patent Citation 1 is applicable only in a case where the angle of the edge surfaces φ satisfies the equation (101), and the method is not applicable in a case where a state in which the angle of the edge surfaces φ does not satisfy the equation (101) occurs.

In addition, in the method disclosed in Patent Citation 2, the length L of the narrow gap section from the weld point to the Vee convergence position depends on the Vee convergence angle, this length L and the Vee convergence angle have a great effect on heating efficiency, and these values easily vary due to the eccentricity of a roller and a material state, such that the welding management accuracy is considered to be low. Particularly, when considering a theoretical equation (the following equation (103)) of the electric resistance welding disclosed in Non Patent Citation 1, since an equivalent heat input Q depends on a geometric Vee convergence angle θ, in Patent Citation 2, the accuracy in the welding management is considered to be low.

$$Q=kPV^{-0.6}I^{-0.55}\theta^{-0.15}I^{-0.85} \quad (103)$$

P: Welding power, θ: Geometrical Vee convergence angle
I: Power supply distance, k: Constant determined by a line configuration The present invention has been made in consideration of the above-described circumstances, and an object of the present invention is to realize electric resistance welding that is free of cold weld defects in which a part of a seamed interface is not melted and is not joined and is free of penetrator defects in which oxides are present on the seamed interface in a wide range of conditions of the edge surfaces.

Methods for Solving the Problem (1) An operation management device for high-frequency resistance welding and induction welding according to an aspect of the present invention performs an operation management for high-frequency resistance welding or induction welding in which a strip-shaped metal plate is formed to have a cylindrical shape in such a manner that both end portions of the metal plate gradually face each other while the metal plate is conveyed, and a Vee convergence section that is a portion at which both of the end portions butt against each other while facing each other is welded. The device includes: a measuring unit that measures a distance L [mm] between a first Vee convergence point at which both of the end portions of the metal plate geometrically come into contact with each other and a second Vee convergence point that is the contact point of both of the end portions of the metal plate, and a Vee convergence angle θ[°] at the first Vee convergence point on the basis of an image of an area including the Vee convergence section; and a determining unit that determines whether or not the distance L [mm] and the Vee convergence angle θ[°] satisfy the following equation (1).

$$L_{min}(\theta/\theta_{st})^{-0.15} \le L \le 35 \quad (1)$$

$L_{min}$ [mm]: Reference distance that is set in advance
$\theta_{st}$[°]: Reference angle that is set in advance (2) The operation management device for high-frequency resistance welding and induction welding according to (1) may further include a control unit that controls an amount of heat input in such a manner that the distance L [mm] and the Vee convergence angle θ[°] that are measured by the measuring unit satisfy the equation (1).

(3) In the operation management device for high-frequency resistance welding and induction welding according to (1) or (2), the measuring unit may include a first detecting unit that binarizes the image to generate a binary image, determines both of the end portions of the metal plate from the binary image, linearly approximates both of the end portions of the metal plate within a predetermined range in the closed direction the formed V-shape to generate two approximated straight-lines, and detects an intersection point of these approximated straight-lines as the first Vee convergence point.

(4) In the operation management device for high-frequency resistance welding and induction welding according to (1) or (2), the measuring unit may include a second detecting unit that binarizes the image to generate a binary image, and detects the second Vee convergence point from the binary image.

(5) In the operation management device for high-frequency resistance welding and induction welding according to (1) or (2), the measuring unit may include: a first detecting unit that binarizes the image to generate a binary image, determines both of the end portions of the metal plate from the binary image, linearly approximates both of the end portions of the metal plate within a predetermined range in the closed direction of the formed V-shape to generate two approximated straight-lines, and detects an intersection point of these approximated straight-lines as the first Vee convergence point; and a second detecting unit that binarizes the image to generate a binary image, and detects the second Vee convergence point from the binary image.

(6) An operation management method for high-frequency resistance welding and induction welding according to another aspect to the present invention performs an operation management for high-frequency resistance welding or induction welding in which a strip-shaped metal plate is formed to have a cylindrical shape in such a manner that both end portions of the metal plate gradually face each other while the metal plate is conveyed, and a Vee convergence section that is a portion at which both of the end portions butt against each other while facing each other is welded. The method includes: imaging an area including the Vee convergence section by an imaging device to form an image; measuring a distance L [mm] between a first Vee convergence point at which both of the end portions of the metal plate geometrically come into contact with each other and a second Vee convergence point that is a contact point of both of the end portions of the metal plate, and a Vee convergence angle θ[°] at the first Vee convergence point on the basis of the image; and determining whether or not the distance L [mm] and the Vee convergence angle θ[°] satisfy the following equation (2).

$$L_{min}(\theta/\theta_{st})^{-0.15} \le L \le 35 \quad (2)$$

$L_{min}$ [mm]: Reference distance that is set in advance
$\theta_{st}$[°]: Reference angle that is set in advance (7) An operation management program for high-frequency resistance welding and induction welding according to still another aspect of the present invention manages high-frequency resistance welding and induction welding in which a strip-shaped metal plate is formed to have a cylindrical shape in such a manner that both end portions of the metal plate gradually face each other while the metal plate is conveyed, and a Vee convergence section that is a portion at which both of the end portions butt against each other while facing each other is welded, by a computer. The program include: a process of measuring a distance L [mm] between a first Vee convergence point at which both of the end portions of the metal plate geometrically come into contact with each other and a second Vee convergence point that is a contact point of both of the end portions of the metal plate, and a Vee convergence angle θ[°] at the first Vee convergence point on the basis of an image of an area including the Vee convergence section; and a process of determining whether or not the distance L [mm] and the Vee convergence angle θ[°] satisfy the following equation (3).

$$L_{min}(\theta/\theta_{st})^{-0.15} \le L \le 35 \quad (3)$$

$L_{min}$ [mm]: Reference distance that is set in advance
θ[°]: Reference angle that is set in advance Effects of the Invention According to the present invention, an operation of electric resistance welding is managed on the basis of conditions considering a variation in a Vee convergence angle with the passage of time, such that electric resistance welding without a cold weld defect and a penetrator defect in a wide range of condition of the edge surfaces may be realized. Particularly, welding may be stably performed without being affected by a variation in the condition of the edge surfaces with the passage of time at the time of operation from welding initiation to welding termination of both end portions of a steel plate.

DETAILED DESCRIPTION OF THE INVENTION

Hereinafter, preferred embodiments of the present invention will be described with reference to the attached drawings.

Figure 1:
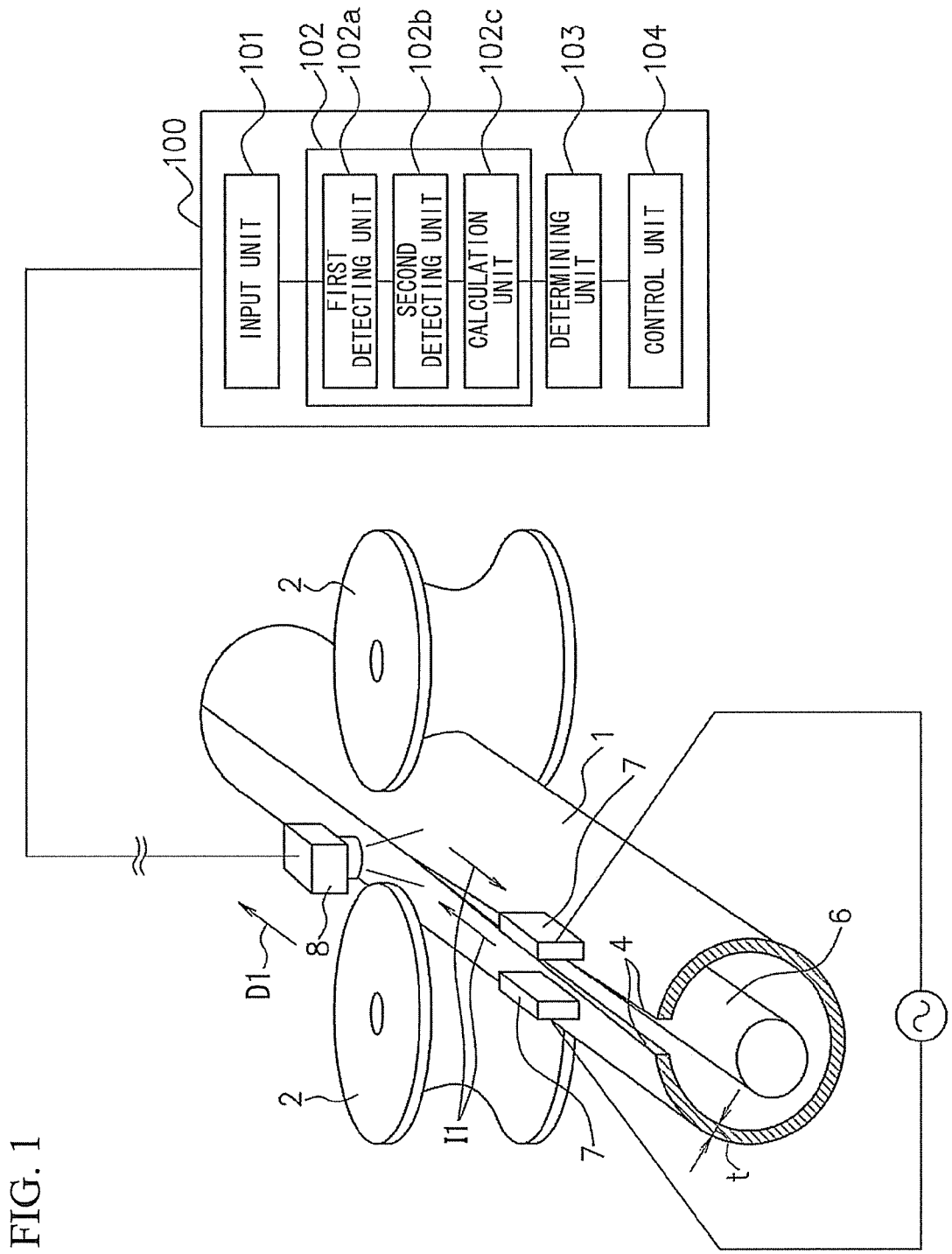
FIG. 1 is a schematic view illustrating a configuration of a facility of manufacturing an electric resistance welded steel pipe and a configuration of an operation management device of electric resistance welding.

First, a facility of manufacturing an electric resistance welded steel pipe will be schematically described with reference to FIG. 1. As shown in FIG. 1, a strip-shaped steel plate (metal plate) 1 is continuously formed to have a cylindrical shape by a roller group (not shown) while being conveyed toward a direction D1. In addition, an impeder 6 is disposed inside the steel plate 1 that is formed to have the cylindrical shape, and an upset force is applied to the steel plate 1 by squeeze rolls 2 while a high-frequency current I1 is made to flow to a weld of the steel plate 1 by a pair of contact tips 7 (that corresponds to high-frequency resistance welding) or induction coils (that is not shown and corresponds to induction welding). As a result, both circumferential end portions 4, 4 (hereinafter, simply referred to as end portions) of the steel plate 1 are heated and melted while being converged into a V-shape toward the direction D1 to butt each other, and therefore the steel plate 1 may be welded (electric resistance welding (ERW)).

Figures 9, 10:
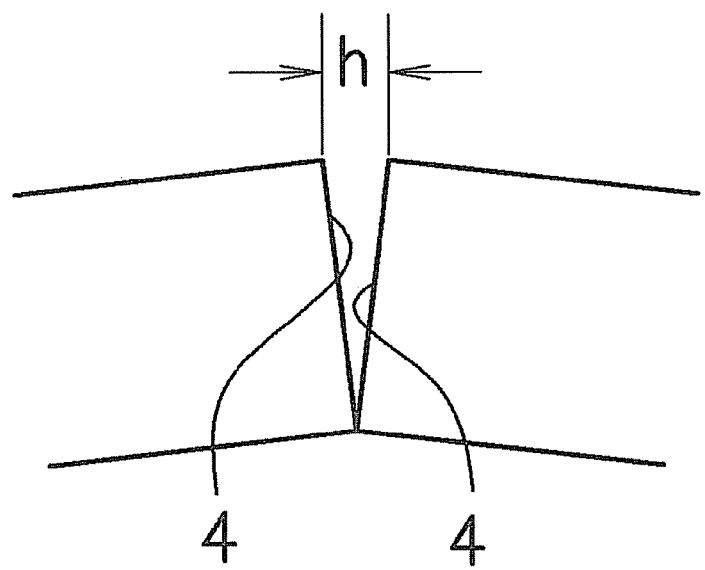
FIG. 9 is a longitudinal cross-sectional view of the end portions of the steel plate to illustrate a distance of the edge surfaces.
FIG. 10 is a view illustrating results of evaluation of the welding quality when welding is performed in each combination of the distance of the edge surfaces and an amount of heat input.

However, at the time of welding, edges of both of the end portions 4, 4 of the steel plate 1 are not necessarily parallel to each other, and as shown in FIG. 9, a gap occurs between both of the butted end portions 4, 4 of the steel plate 1. As the maximum length dimension (hereinafter, referred to as a distance of the edge surfaces) h of the gap is large, normal welding may be impossible. Furthermore, the distance of the edge surfaces h may vary with the passage of time at the time of welding, and therefore the welding quality may decrease at a position of the weld with a long distance of the edge surfaces h. In addition, in FIG. 9, a state in which the gap occurs at an upper side of a steel (an outer surface side of a steel pipe) is described, but the gap may occur at a lower side (an inner side of a steel pipe).

Therefore, an evaluation of the welding quality (Charpy impact test under a high temperature of substantially 160° C.) was performed by changing a condition of both of the end portions 4, 4 of the steel plate 1 and the amount of heat input. As a result thereof, even when the distance of the edge surfaces h (refer to FIG. 9) exceeded 0.3 [mm], the welding was performed normally by controlling the amount of heat input. FIG. 10 shows results of evaluation of the welding quality in a case where the welding was performed with a combination of the distance of the edge surfaces h (0, 0.3, 0.6, 0.9 [mm]) and the amount of heat input (weld states A to D in FIG. 10 correspond to small amount of heat input to large amount of heat input, respectively). In FIG. 10, "no good" indicates that a cold weld defect or a penetrator defect occurs, and "good" indicates that no defects occur and the welding is performed normally. In the weld state A, due to deficiency of the heat input, the cold weld defect caused by deficiency of melting occurred. Particularly, as the distance of the edge surfaces h was lengthened, the frequency of occurrence of the cold weld defect increased. In addition, in the weld state B, when the distance of the edge surfaces h was short (when the edge surfaces close to a parallel state), the welding was performed normally, but the distance of the edge surfaces h was long, and a cold weld defect occurred. Furthermore, in the weld state C, the amount of heat input was appropriately controlled, such that even when the distance of the edge surfaces h exceeded 0.3 [mm], the welding was performed normally. In addition, in the weld state D, due to an excessive heat input, the cold weld defect and the penetrator defect, which occur due to pressure welding in an oxidized state, occurred. In an actual operation, due to a variation (variation with the passage of time) in a plate thickness or a position of both of the end faces 4, 4 of the steel plate 1 at the time of butting or the like, the distance of the edge surfaces h may exceed 0.3 [mm], such that the weld state C is an ideal weld state.

That is, the weld state A is a weld state with a small amount of heat input in which the cold weld defect occurs, the weld state B is a weld state with a small amount of heat input (with an amount of heat input larger than that in the weld state A) in which the cold weld defect occurs when the distance of the edge surfaces h at the time of operation increases. The weld state C is a weld state with an optimal amount of heat input (with an amount of heat input larger than that in the weld state B) in which the welding may be performed normally without depending on the distance of the edge surfaces at the time of operation. In addition, the weld state D is a weld state with an excessive heat input (with an amount of heat input larger than that in the weld state C) in which the cold weld defect and the penetrator defect occur. In addition, overall evaluation in FIG. 10 represents evaluation considering a variation in the distance of the edge surfaces h with the passage of time at the time of actual operation. As shown in FIG. 10, in the weld state A, the weld state B, and the weld state D, the above-described defect occurs, but in the weld state C, the welding may be reliably performed at the time of actual operation.

The inventors found that conditions, under which the welding may be performed normally even when the distance of the edge surfaces h exceeds 0.3 [mm] as described above, correlate to a phenomenon in which the Vee convergence angle varies with two phases (two-phased convergence phenomenon). The two-phased convergence phenomenon is a phenomenon that is observed as if the end portion 4 recedes because the central portion in a plate thickness direction is melted and discharged, when melted portions in the plate thickness direction of the end portions 4 of the steel plate 1 butt each other while being discharged (refer to FIG. 8B).

Figure 8A:
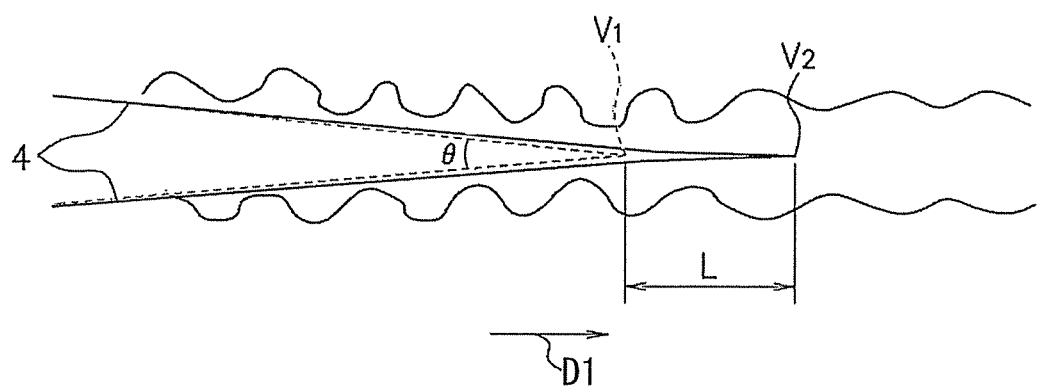
FIG. 8A is a schematic top plan view of the steel plate to illustrate the two-phased convergence phenomenon.

When a self-luminescent pattern in an area including the Vee convergence section was imaged from an upper side of the steel plate 1 with high accuracy and without image lag (under conditions of an image resolution of: 60 [μm/pixel] and an exposure time of: $1/10000$ [seconds]) and a Vee convergence point was measured with high accuracy, the two-phased convergence phenomenon was observed. When the two-phased convergence phenomenon occurs, it can be understood that a geometric Vee convergence point $V_1$ (hereinafter, referred to as a first Vee convergence point) is present on an upstream side in a conveyance direction D1 as shown in FIG. 8A, and a convergence point $V_2$ (hereinafter, referred to as a second Vee convergence point) that is a contact point is present on a downstream side. As represented as a broken line in FIG. 8A, the first Vee convergence point is a point at which both of the end portions 4, 4 that converge in a V-shape geometrically come into contact with each other. That is, the first Vee convergence point is an intersection point of tangential lines (extended lines) of both of the upstream side end portions 4, 4 that can be linearly approximated. In addition, the second Vee convergence point is a point at which both of the end portions 4, 4 that converge in a V-shape physically butt each other (come into contact with each other). In addition, the weld point (point at which solidification starts to begin) is present at a further downstream side compared to the second Vee convergence point.

Figure 7A:
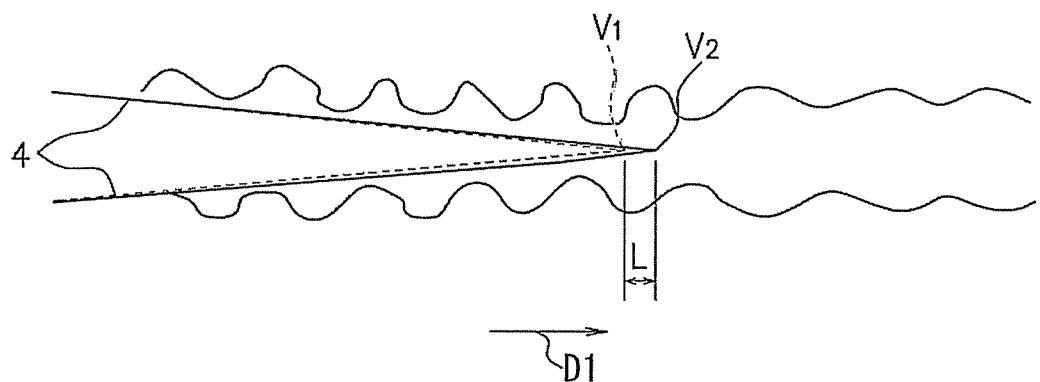
FIG. 7A is a schematic top plan view of a steel plate to illustrate two-phased convergence phenomenon.
Figure 7B:
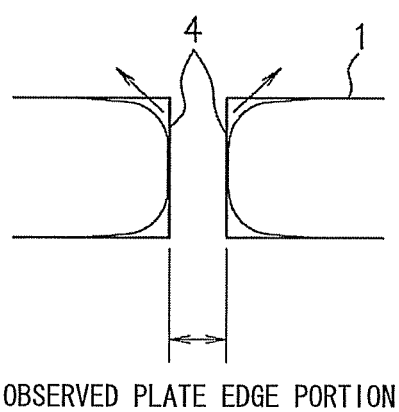
FIG. 7B is a longitudinal cross-sectional view of end portions of a steel plate to illustrate the two-phased convergence phenomenon.
Figure 8B:
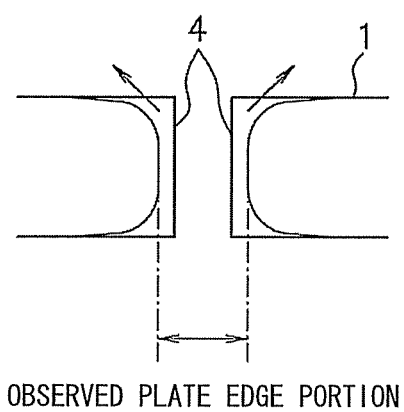
FIG. 8B is a longitudinal cross-sectional view of the end portions of the steel plate to illustrate the two-phased convergence phenomenon.

Furthermore, it was confirmed that the distance L between the first Vee convergence point and the second Vee convergence point varies in response to the amount of heat input, and as the amount of heat input increases, the first Vee convergence point and the second Vee convergence point are distant from each other. FIGS. 7A and 7B illustrate the two-phased convergence phenomenon observed in the weld state B, and as shown in FIG. 7A, the first Vee convergence point and the second Vee convergence point are close to each other (substantially consistent with each other). In this case, as shown in FIG. 7B, melting may be insufficient at the central portion of the end portion 4 of the steel plate 1 in the plate thickness direction, and therefore the cold weld defect may occur. Conversely, FIGS. 8A and 8B illustrate the two-phased convergence phenomenon observed in the weld state C, and as shown in FIG. 8A, the first Vee convergence point and the second Vee convergence point are distant from each other. In this case, as shown in FIG. 8B, the melting in the central portion in the plate thickness direction of the end portion 4 of the steel plate 1 becomes appropriate, and therefore the end portions 4,4 of the steel plate 1 may be normally welded. In addition, arrows shown in FIGS. 7B and 8B illustrate a state in which the end portions 4, 4 of the steel plate 1 are melted and the melted portions are discharged.

As described above, it was found that the distance L between the first Vee convergence point and the second Vee convergence point that are exhibited in the two-phased convergence phenomenon correlates with a melting state of the central portion in the plate thickness direction of the end portion 4 of the steel plate 1. The present invention continuously manages an operation of the electric resistance welding by determining an appropriate range of the distance L on the basis of the above-described findings, and by measuring the distance L with accuracy through image processing.

FIG. 1 shows a functional configuration of an operation management device 100 of the electric resistance welding. As shown in FIG. 1, an imaging device 8 is disposed above the steel plate 1 to capture a self-luminescent pattern (a radiation pattern) in an area including the Vee convergence section of the steel plate 1. As the imaging device 8, for example, a 3CCD color camera of 1600×1200 pixels is used and the self-luminescent pattern is imaged under conditions in which an imaging area is 50 [mm]×100 [mm], resolution is 50 [μm/pixel], a frame rate is 40 [fps], and an exposure time is 1/10000 [seconds]. Here, for an image processing described later, an imaging area is set in such a manner that a position of the second Vee convergence point in a captured image is located, for example, at substantially ⅓ of a width of imaging area in the conveyance direction D1 from the downstream side of the conveyance direction D1 at the time of normal operation.

The operation management device 100 of the electric resistance welding includes an input unit 101, a measuring unit 102, a determining unit 103, and a control unit 104. Image data imaged by the imaging device 8 is input to the input unit 101.

The measuring unit 102 measures the distance L [mm] between the first Vee convergence point and the second Vee convergence point, and the Vee convergence angle θ[°] at the first Vee convergence point on the basis of the image data input to the input unit 101. The measuring unit 102 includes a first detecting unit 102a, a second detecting unit 102b, and a calculation unit 102c. The first detecting unit 102a binarizes the image data input to the input unit 101 to generate a binary image, determines both of the end portions 4, 4 of the steel plate 1 from the binary image, linearly approximates both of the end portions 4, 4 of the steel plate 1 within a predetermined range in a closed direction of a V-shape to generate two approximated straight-lines, and detects an intersection point of these approximated straight-lines as the first Vee convergence point. In addition, the second detecting unit 102b binarizes the image data input to the input unit 101 to generate a binary image, and detects the second Vee convergence point from the binary image. Furthermore, the calculation unit 102c acquires the distance L [mm] between the first Vee convergence point and the second Vee convergence point, and a Vee convergence angle θ[°] at the first Vee convergence point on the basis of the first Vee convergence point detected by the first detecting unit 102a and the second Vee convergence point detected by the second detecting unit 102b.

The determining unit 103 determines whether or not the distance L [mm] and the Vee convergence angle θ[°] measured by the measuring unit 102 satisfy the following equation (4).

$$L_{min}(\theta/\theta_{st})^{-0.15} \leq L \leq 35 \tag{4}$$

$L_{min}$: Reference distance that is set in advance
$\theta_{st}$: Reference angle that is set in advance The lower limit $L_{min}(\theta/\theta_{st})^{-0.15}$ is a value obtained by calibrating the reference distance $L_{min}$ that is experimentally obtained on the basis of a theory in which an amount of heat input is proportional to $(\theta/\theta_{st})^{-0.15}$. In addition, when the distance L [mm] between the first Vee convergence point and the second Vee convergence point becomes shorter than $L_{min}(\theta/\theta_{st})^{-0.15}$ [mm] the weld state at the time of operation enters the weld state A or the weld state B in which the heat input is insufficient. $L_{min}$ and $\theta_{st}$ are set in response to the material of the steel plate 1, the plate thickness, and the pipe diameter. When a description is made with reference to carbon steel as an example, $L_{min}$ and $\theta_{st}$ may be set in a detailed manner in such a manner that for example, when the plate thickness is less than 4 [mm], $\theta_{st}$ is 3.5[°] with $L_{min}$ of 3.5 [mm], when the plate thickness is equal to or greater than 4 [mm] and less than 10 [mm], $\theta_{st}$ is 5[°] with $L_{min}$ of 5 [mm], and when the plate thickness is 10 [mm] or more, $\theta_{st}$ is 7[°] with $L_{min}$ of 6.5 [mm]. In addition, for example, $L_{min}$ and $\theta_{st}$ may be uniformly set without depending on the plate thickness in such a manner that $\theta_{st}$ is 5[°] with $L_{min}$ of 5 [mm]. With respect to a steel of another material, $L_{min}$ and $\theta_{st}$ may be also set similarly. In this manner, when the distance L is controlled to be equal to or more than the lower limit $L_{min}(\theta/\theta_{st})^{-0.15}$, even when the variation in the distance of the edge surfaces h with the passage of time (for example, a temporal increase) is present at the time of an actual operation, the cold weld defect due to a deficiency of heat input may be prevented from occurring.

In addition, the upper limit of 35 is a value that can be experimentally obtained, and when the distance L [mm] between the first Vee convergence point and the second Vee convergence point becomes longer than 35 [mm], this leads to the weld state D of the excessive heat input. That is, when the distance L becomes longer than 35 [mm], a frequency of occurrence of oxides (penetrator defect) increases as the distance L increases. Therefore, when the distance L is controlled to be 35 [mm] or less, the penetrator defect due to the excessive heat input may be prevented from occurring at the time of an actual operation.

In a case where the determining unit 103 determines that the distance L [mm] and the Vee convergence angle θ[°] do not satisfy the above-described equation (4), the control unit 104 controls the amount of heat input by changing an application voltage (or a frequency) to a welding device such as the contact tips 7 and the induction coils so as to satisfy the above-described equation (4). That is, the amount of heat input is controlled in order for the distance L to satisfy the above-described equation (4) in such a manner that when the distance L is less than $L_{min}(\theta/\theta_{st})^{-0.15}$, the amount of heat input is raised, and when the distance L exceeds 35 [mm], the amount of heat input is lowered. In addition, while the distance L satisfies the above-described equation (4), the control may be performed without changing the amount of heat input, or the amount of heat input may be controlled to a determined value satisfying the above-described equation (4). In addition, in a case where the amount of heat input is raised when the distance L is less than $L_{min}(\theta/\theta_{st})^{-0.15}$, since the Vee convergence angle θ increases in addition to the increase in the distance L, the lower limit of $L_{min}(\theta/\theta_{st})^{-0.15}$ decreases and therefore the welding may be stably performed without causing divergence of processing.

Figure 2:
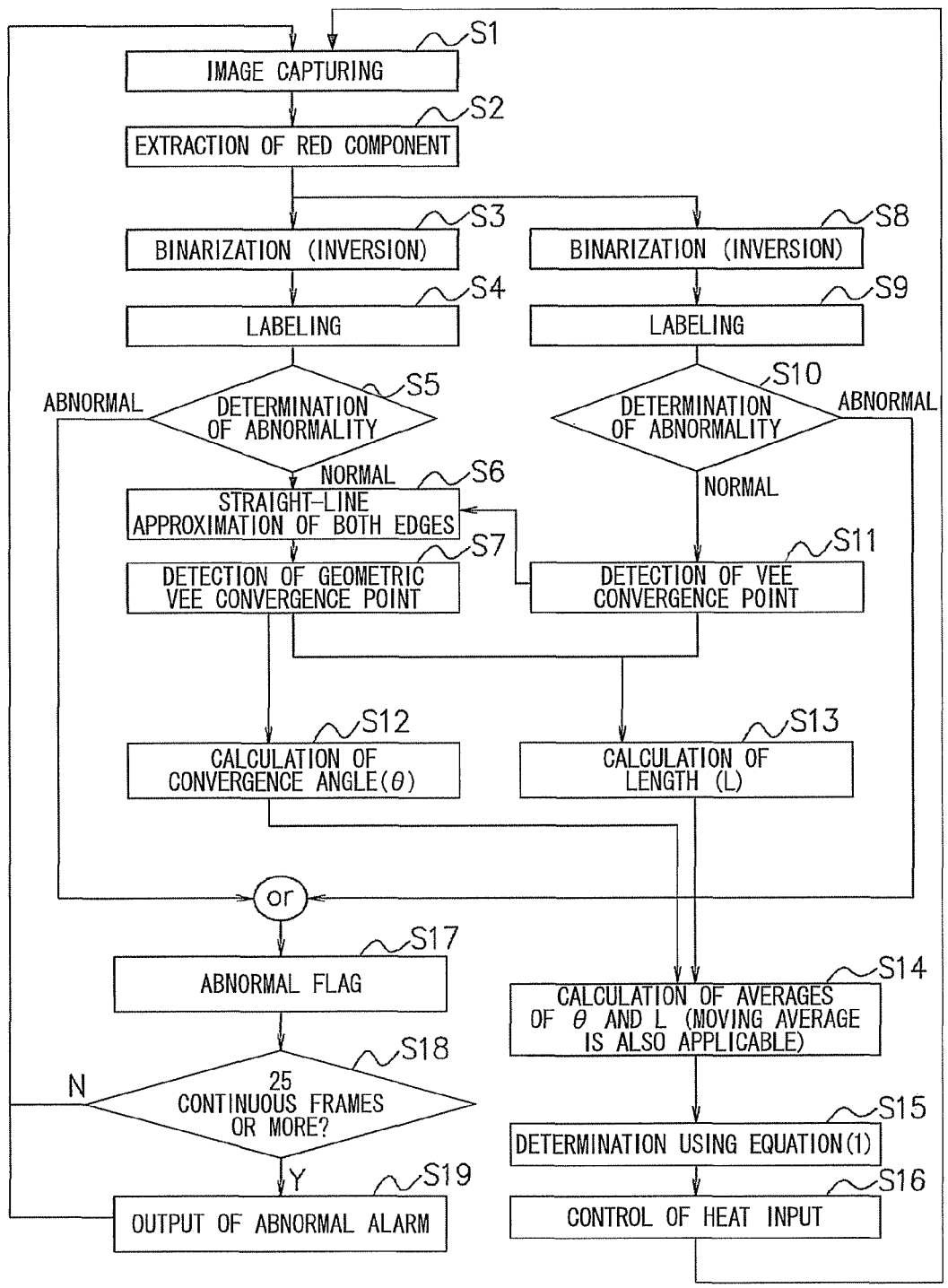
FIG. 2 is a flowchart illustrating an operation management method by the operation management device of the electric resistance welding.
Figure 3:
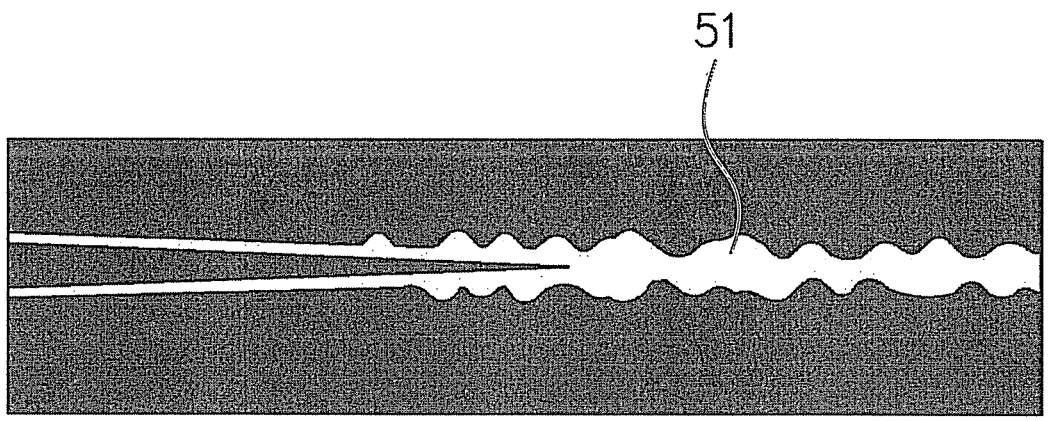
FIG. 3 is a schematic view illustrating an image photographed by an imaging device.

FIG. 2 shows an operation management method by the operation management device 100 of the electric resistance welding. The imaging by the imaging device 8 is continuously performed with a constant time interval, and one sheet of image captured at any timing is called a frame. When the image data is input to the input unit 101 from the imaging device 8 (step S1), a red component (a wavelength of 590 to 680 nm) is extracted from the image data in the input unit 101 or the measuring unit 102 so as to clarify contrast (step S2). FIG. 3 shows a schematic view of an image photographed by the imaging device 8. In addition, in the following description, in the image shown in FIG. 3, FIGS. 4A to 4D, FIG. 5, and FIG. 6, a vertical direction (circumferential direction) is expressed as a Y direction, and a lateral direction (conveyance direction) is expressed as an X direction. In the image obtained by the imaging device 8, a high heat area 51 in which a brightness level is high appears along both of the end portions 4, 4 of the steel plate 1, and a wave-shaped pattern that is formed due to discharge of a melted portion of both of the end portions 4, 4 appears on the downstream side in the conveyance direction (X direction).

Figure 4A:
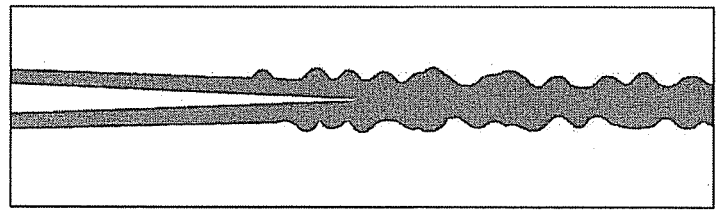
FIG. 4A is a schematic view illustrating a binary image that is processed by a measuring unit.
Figure 4B:
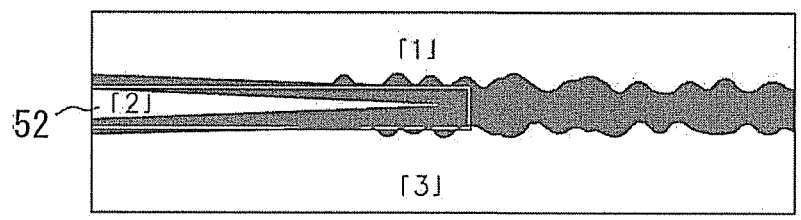
FIG. 4B is a schematic view illustrating each blob in the binary image.
Figure 4C:
FIG. 4C is a schematic view illustrating a blob of an extracted Vee convergence section.

The first detecting unit 102a of the measuring unit 102 binarizes (inverts) the image data in which the red component is extracted in step S2 (step S3). Here, "0" is substituted to a pixel in which the brightness level is a predetermined value or more, and "1" is substituted to a pixel in which the brightness level is less than a predetermined value. FIG. 4A shows a schematic view of the binary image.

Figure 6:
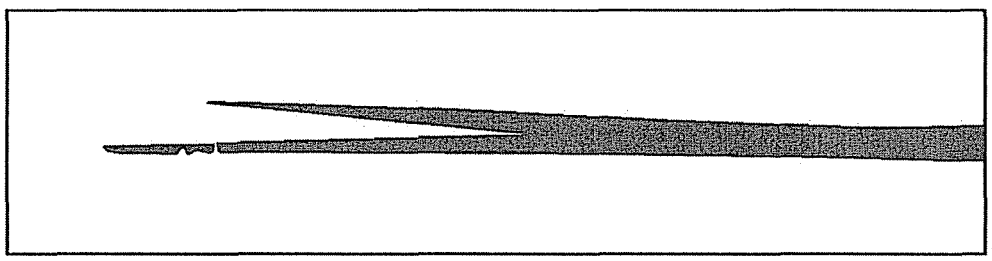
FIG. 6 is a schematic view illustrating an example of a binary image from which the blob of the Vee convergence section is not extracted.

Next, the first detecting unit 102a performs a labeling to attach a label for each blob in the binary image (refer to FIG. 4B) (step S4), and determines whether or not a blob that is consistent with a predetermined condition is extracted (step S5). Here, the blob is an individual area in which any one of adjacent eight pixels including four upper, lower, left, and right pixels and four diagonal pixels to which a pixel of "1" is adjacent in the binary image is "1", and pixels are connected to form one lump (here, a lump of pixels of "1"). In addition, in the labeling, the individual blob is identified, a label number is given to the individual blob, a specific blob is extracted, and information about a position (the maximum point and the minimum point in the X coordinate, and the maximum point and the minimum point in the Y coordinate) in an image of the specific blob, and a width, a length, an area, or the like of the image of the specific blob is extracted. For example, in FIG. 4B, labels of [1], [2], and [3] are given to three blobs, respectively. In step S5, when a blob that is consistent with a predetermined condition is present, this blob (here, the label [2]) is extracted as a blob 52 of the Vee convergence section that is a section in which both of the circumferential end portions 4,4 converge into V-shape (refer to FIG. 4C). Shape information such as a coordinate and an area is acquired with respect to the blob 52. For example, in the binary image shown in FIG. 4A, when a blob, which comes into contact with the left end and has a predetermined area condition, is present, this blob is extracted as the blob 52 of the Vee convergence section. As the predetermined area condition, for example, conditions such as a condition in which an actual dimension of the blob area is 15 to 150 mm² or a condition in which an actual dimension of a circumscribed rectangular block is 25 to 320 mm² may be set. In addition, as the predetermined area condition, a plurality of conditions may be combined. When a blob that is consistent with a predetermined condition is not extracted in step S5, the process proceeds to step S17. For example, in a case where the amount of heat input is too small, as shown in FIG. 6, since the blob of the Vee convergence section is not extracted, the process proceeds to step S17.

Figure 4D:
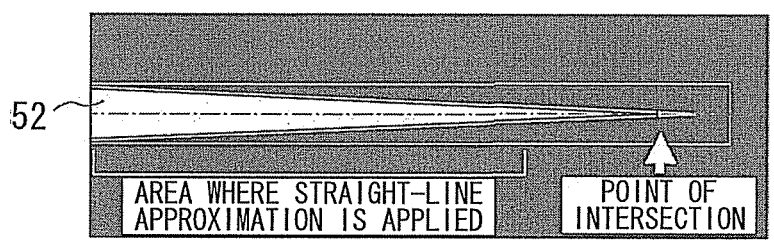
FIG. 4D is a schematic view illustrating an example of a method of determining a geometric Vee convergence point $V_1$.

Next, the first detecting unit 102a searches both of the circumferential end portions 4, 4 of the steel plate 1 from the blob 52 of the Vee convergence section, which is extracted in steps S4 and S5. As shown in FIG. 4D, toward +Y direction and −Y direction from a point on a straight line (indicated by chain line in FIG. 4D) that passes through the most downstream point (a second Vee convergence point that is detected in the following step S11) of the blob 52 of the Vee convergence section in the conveyance direction and that is parallel to the X direction, points at which a pixel value becomes "0" ("1" to "0") for the first time are searched, respectively, and these points are determined as the end portions 4 of the steel plate 1. This searching process is performed within a predetermined range in a closed direction (X direction) of the V-shape, for example, within ⅔ range from the left end in a range from the left end (upstream side in the conveyance direction) of the binary image to the front end of the blob 52 of the Vee convergence section. In addition, within this predetermined range, the end portions 4 of the steel plate 1 are linearly approximated (step S6), and an intersection point of the approximated straight lines is detected as the first Vee convergence point (step S7). In addition, it is preferable that the predetermined range be set in an appropriate range in response to operation conditions instead of being set always to the same reference (for example, the "⅔ range from the left end"). For example, in a case where the position of the first Vee convergence point may move to the upstream side in the conveyance direction according to the operation conditions, it is preferable that the predetermined range be set to a relatively small value (for example, "½ range from the left end").

In addition, when searching the end portions 4 of the steel plate 1, for example, toward an inner side (central portion) from vertical positions (the uppermost position and the lowest position) of an image shown in FIG. 4D, points at which a pixel value becomes "1" ("0" to "1") for the first time may be searched. However, since the blob 52 of the Vee convergence section appears in the vicinity of the center of the image in the vertical direction (Y direction), when the search is started from the uppermost position and the lowest position of the image, the number of unnecessary processes is increased. Therefore, a processing time is shortened by searching the points, at which the pixel value becomes "0" ("1" to "0") for the first time, toward the +Y direction and −Y direction from the inner side of the blob 52 of the Vee convergence section as described above. In addition, even when the points, at which the pixel value becomes "1" ("0" to "1") for the first time, are searched from the vertical positions of the image toward the inner side, a Y-directional position of a large width section (the left end of the image) of the blob 52 of the Vee convergence section may be determined by the labeling, such that when points, at which the pixel value becomes "1" ("0" to "1") for the first time, are searched from the Y-directional position or the vicinity thereof toward the inner side, the processing time may be shortened.

Together with the processes in steps S3 to S7, the second detecting unit 102b of the measuring unit 102 binarizes (inverts) the image data in which the red component is extracted in step S2 (step S8). Here, "0" is substituted to a pixel in which the brightness level is a predetermined value or more, and "1" is substituted to a pixel in which the brightness level is less than a predetermined value.

Figure 5:
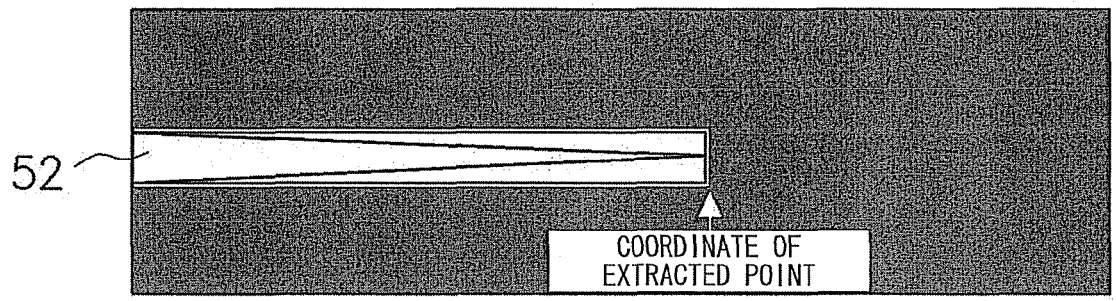
FIG. 5 is a schematic view illustrating an example of a method of determining a Vee convergence point $V_2$ that is a contact point.

Next, the second detecting unit 102b performs a labeling to attach a label for each blob in the binary image similarly to the first detecting unit 102a (step S9), and determines whether or not a blob that is consistent with a predetermined condition is extracted (step S10). In step S10, when a blob that is consistent with a predetermined condition is present, this blob is extracted as the blob 52 of the Vee convergence section, and shape information such as a coordinate and an area with respect to the blob is acquired. In addition, as shown in FIG. 5, the front end of the blob 52 of the Vee convergence section in the X direction is detected as the second Vee convergence point (step S11). In this case, when a blob that is consistent with a predetermined condition is not extracted in step S10, the process also proceeds to step S17.

In this embodiment, the binarization is performed by each of the first detecting unit 102a and the second detecting unit 102b, but this is for setting a threshold value of the binarization to an appropriate value by each of the detecting units (processes). Naturally, processes such as the binarization and the labeling may be integrated between the first detecting unit 102a and the second detecting unit 102b as long as the threshold value of the binarization may be set similarly with respect to each of the detecting units.

As described above, after the first Vee convergence point and the second Vee convergence point are detected, the calculation unit 102c acquires the distance L [mm] between the first Vee convergence point and the second Vee convergence point (step S13), and acquires a Vee convergence angle θ[°] at the geometric Vee convergence point (step S12).

Next, the determining unit 103 performs an average calculation of the distance L [mm] and the Vee convergence angle θ[°] that are measured for each frame by the measuring unit 102 (step S14). For example, average calculation, preferably, moving average calculation is performed with respect to the distance L [mm] and the Vee convergence angle θ[°] that are obtained by repeating steps S1 to S13 over 16 times. Then, in step S14, it is determined whether or not the distance L [mm] and the Vee convergence angle θ[°] that are obtained by the average calculation in step S14 satisfy the above-described equation (4) (step S15).

In a case where the determining unit 103 determines that the distance L [mm] and the Vee convergence angle θ[°] do not satisfy the above-described equation (4) in step S15, the control unit 104 controls the amount of heat input by changing an application voltage (or a frequency) to a welding device such as the contact tips 7 and the induction coils so as to satisfy the above-described equation (4) (step S16). That is, the amount of heat input is controlled in order for the above-described equation (4) to be satisfied in such a manner that when the distance L is less than $L_{min}(θ/θ_{st})^{-0.15}$, the amount of heat input is raised, and when the distance L becomes 35 [mm], the amount of heat input is lowered. In addition, in a case where the distance L satisfies the above-described equation (4), the amount of heat input is controlled in such a manner that the amount of heat input is maintained as it is. After step S16, the process returns again to step S1, and the control of the amount of heat input is repeated until the welding is completed. In addition, it is preferable that the processes from step S1 to step S16 be performed for each constant interval (for example, for each imaging interval).

In addition, in step S17, an abnormal flag is set. Then, in step S18, it is determined whether or not the abnormal flag is set in succession, for example, for 25 frames or more. When the number of continuous frames of the abnormal flags does not reach, for example, 25 times in step S18 ("N"), the process returns again to step S1. In addition, when the abnormal flags are set in succession, for example, for 25 frames or more in step S18 ("Y"), an abnormal alarm is output in step S19. Furthermore, after this step S19, the process returns again to step S1.

In addition, the average times or moving average times of the distance L [mm] and the Vee convergence angle θ[°] that are detected is not limited to 16 times, and may be appropriately changed in response to a welding device or a kind of steel plate. Similarly, the number of continuous frames of the abnormal flags to output the abnormal alarm is not limited to 25 frames and may be appropriately changed in response to a welding device or a kind of steel plate.

As described above, in this embodiment, in a case where the distance of the edge surfaces h at the time of operation varies (increases) with the passage time, since not only the cold weld defect or the penetrator defect may be prevented, but also the amount of heat input may be controlled only using the distance L and the Vee convergence angle θ, the welding may be performed in a reliable and efficient manner.

Furthermore, a steel pipe was manufactured from a steel plate using a manufacturing facility of the electric resistance welded steel pipe in FIG. 1.

In Table 1, examples (Examples) satisfying the above-described equation (4) and examples (Comparative Examples) not satisfying the above-described equation (4) are shown.

Here, t represents the plate thickness [mm] of the steel plate, V represents a welding speed [mpm], and EpIp represents input power [kW]. For example, in Example No. 1, since the lower limit $L_{min}(θ/θ_{st})^{-0.15}$ was 4.9 [mm] with the distance L of 29.7 [mm], the distance L satisfied the above-described equation (4) (4.9≤29.7≤35). In addition, for example, in Example No. 11, since the lower limit $L_{min}(θ/θ_{st})^{-0.15}$ was 4.3 [mm] with the distance L of 34.8 [mm], the distance L was close to the upper limit of 35 [mm], but the distance L satisfied the above-described equation (4) (4.3≤34.8≤35). Similarly, in Example Nos. 3 to 13, the distance L satisfied the above-described equation (4). Therefore, in these Example Nos. 1 to 13, the weld phenomenon type was the ideal weld state C.

On the other hand, for example, in Comparative Example No. 14, the distance L was 0.2 [mm], and was smaller than the lower limit $L_{min}(θ/θ_{st})^{-0.15}$ of 4.9 [mm]. The weld phenomenon type in this case was the weld state A in which due to deficiency of the heat input, a cold weld defect caused by deficiency of melting may occur. Similarly, in Comparative Example Nos. 15, 16, 18, 19, 22, 23, 25, 26, 27, 29, and 30, since the distance L was shorter than the lower limit $L_{min}(θ/θ_{st})^{-0.15}$, the weld phenomenon type was the weld state A or the weld state B in which the heat input is insufficient.

In addition, for example, in Comparative Example No. 31, the distance L was 37.6 [mm], and was longer than the upper limit of 35 [mm]. The weld phenomenon type in this case was the weld state D in which due to the excessive heat input, the cold weld defect and the penetrator defect, which occurs because the weld is pressure-welded in a partially oxidized state, occurred. Similarly, in Comparative Examples No. 17, 20, 21, 24, 28, and 32, since the distance L was larger than the upper limit of 35 [mm], the weld phenomenon was the weld state D of the excessive heat input.

TABLE 1

|  | No. | t (mm) | V (mpm) | EpIp (kW) | θ (°) | L (mm) | $L_{min}$ (mm) | $θ_{st}$ (°) | $L_{min}(θ/θ_{st})^{-0.15}$ (mm) | Weld phenomenon type |
|---|---|---|---|---|---|---|---|---|---|---|
| Example | 1 | 4.8 | 20 | 244 | 5.0 | 29.7 | 5.0 | 4.5 | 4.9 | C |
|  | 2 | 4.8 | 20 | 284 | 5.0 | 34.2 | 5.0 | 4.5 | 4.9 | C |
|  | 3 | 4.8 | 40 | 420 | 4.8 | 33.8 | 5.0 | 4.5 | 5.0 | C |
|  | 4 | 4.8 | 40 | 461 | 5.0 | 31.5 | 5.0 | 4.5 | 4.9 | C |
|  | 5 | 4.8 | 50 | 475 | 5.0 | 11.5 | 5.0 | 4.5 | 4.9 | C |
|  | 6 | 4.8 | 50 | 501 | 5.0 | 21.6 | 5.0 | 4.5 | 4.9 | C |
|  | 7 | 4.8 | 50 | 528 | 4.5 | 32.3 | 5.0 | 4.5 | 5.0 | C |
|  | 8 | 9.5 | 10 | 253 | 6.2 | 18.1 | 4.5 | 6.0 | 4.5 | C |
|  | 9 | 9.5 | 20 | 445 | 6.0 | 22.4 | 4.5 | 6.0 | 4.5 | C |
|  | 10 | 9.5 | 25 | 495 | 6.5 | 7.2 | 4.5 | 6.0 | 4.4 | C |
|  | 11 | 9.5 | 25 | 537 | 6.5 | 27.2 | 4.5 | 6.0 | 4.4 | C |
|  | 12 | 12.9 | 10 | 310 | 5.5 | 26.3 | 4.0 | 7.5 | 4.2 | C |
|  | 13 | 12.9 | 10 | 329 | 5.0 | 34.8 | 4.0 | 7.5 | 4.3 | C |
| Comparative | 14 | 4.8 | 20 | 212 | 5.5 | 0.2 | 5.0 | 4.5 | 4.9 | A |
| Example | 15 | 4.8 | 20 | 227 | 5.0 | 0.1 | 5.0 | 4.5 | 4.9 | A |
|  | 16 | 4.8 | 20 | 235 | 5.0 | 3.8 | 5.0 | 4.5 | 4.9 | B |
|  | 17 | 4.8 | 20 | 360 | 4.0 | 48.0 | 5.0 | 4.5 | 5.1 | D |
|  | 18 | 4.8 | 40 | 397 | 4.8 | 0.0 | 5.0 | 4.5 | 5.0 | A |
|  | 19 | 4.8 | 40 | 414 | 4.8 | 3.2 | 5.0 | 4.5 | 5.0 | B |
|  | 20 | 4.8 | 40 | 504 | 4.8 | 37.8 | 5.0 | 4.5 | 5.0 | D |
|  | 21 | 4.8 | 40 | 523 | 4.0 | 54.4 | 5.0 | 4.5 | 5.1 | D |
|  | 22 | 4.8 | 50 | 432 | 5.0 | 0.4 | 5.0 | 4.5 | 4.9 | A |
|  | 23 | 4.8 | 50 | 442 | 5.0 | 2.0 | 5.0 | 4.5 | 4.9 | B |
|  | 24 | 9.5 | 10 | 271 | 6.5 | 43.7 | 4.5 | 6.0 | 4.4 | D |
|  | 25 | 9.5 | 20 | 374 | 6.5 | 1.3 | 4.5 | 6.0 | 4.4 | A |
|  | 26 | 9.5 | 25 | 452 | 6.5 | 2.1 | 4.5 | 6.0 | 4.4 | A |
|  | 27 | 9.5 | 25 | 468 | 6.5 | 4.1 | 4.5 | 6.0 | 4.4 | B |
|  | 28 | 9.5 | 25 | 568 | 6.5 | 52.6 | 4.5 | 6.0 | 4.4 | D |
|  | 29 | 12.9 | 10 | 284 | 5.5 | 0.2 | 4.0 | 7.5 | 4.2 | A |
|  | 30 | 12.9 | 10 | 294 | 5.5 | 3.9 | 4.0 | 7.5 | 4.2 | B |
|  | 31 | 12.9 | 10 | 312 | 5.5 | 37.6 | 4.0 | 7.5 | 4.2 | D |
|  | 32 | 12.9 | 10 | 337 | 5.0 | 54.0 | 4.0 | 7.5 | 4.3 | D |

As described above, since the operation of the electric resistance welding is managed on the basis of the equation (4) considering the variation in the Vee convergence angle θ with the passage of time, even in a condition of the edge surfaces in which the distance of the edge surfaces h exceeds 0.3 [mm], the electric resistance welding that is free of cold weld defects and penetrator defects may be realized.

Specifically, the operation management device of the electric resistance welding according to the present invention may be made up by a computer system provided with CPU, ROM, RAM, or the like, and is realized when the CPU executes a program. In addition, the operation management device of the electric resistance welding according to the present invention may be made up of one device or a plurality of devices.

In addition, the object of the present invention may be accomplished by supplying a storage medium, in which the program code of software realizing an operation management function of the above-described electric resistance welding of the strip is recorded, to a system or a device. In this case, the program code itself, which is read-out from the storage medium, realizes the function of the above-described embodiment, and the program code itself and the storage medium in which the program code is stored can make up the present invention. As the storage medium that supplies the program code, for example, a flexible disk, a hard disk, an optical disc, a magneto-optical disc, a CD-ROM, a CD-R, a magnetic tape, a non-volatile memory card, a ROM, or the like may be used.

INDUSTRIAL APPLICABILITY

The operation of the electric resistance welding is managed on the basis of conditions considering a variation in the Vee convergence angle with the passage of time, such that the electric resistance welding, which is free of cold weld defects and penetrator defects, may be realized in a wide range of conditions of the edge surfaces.

REFERENCE SYMBOL LIST

101: Input unit
102: Measuring unit
102*a*: First detecting unit
102*b*: Second detecting unit
102*c*: Calculation unit
103: Determining unit
104: Control unit

What is claimed is:
1. An operation management device for high-frequency resistance welding and induction welding, which performs an operation management for high-frequency resistance welding or induction welding in which a strip-shaped metal plate is formed to have a cylindrical shape in such a manner that both end portions of the metal plate gradually face each other while the metal plate is conveyed, and a Vee convergence section that is a portion at which both of the end portions butt against each other while facing each other is welded, the device comprising:

a measuring unit that measures a distance L [mm] between a first Vee convergence point at which both of the end portions of the metal plate geometrically come into contact with each other and a second Vee convergence point that is a contact point of both of the end portions of the metal plate, and a Vee convergence angle $\theta[°]$ at the first Vee convergence point based on an image of an area including the Vee convergence section, wherein the measuring unit includes:

a first detecting unit that binarizes the image to generate a binary image, determines both of the end portions of the metal plate from the binary image, linearly approximates both of the end portions of the metal plate within a predetermined range in a closed direction of a formed V-shape to generate two approximated straight-lines, and detects an intersection point of the approximated straight-lines as the first Vee convergence point;

a second detecting unit that binarizes the image to generate a binary image, and detects the second Vee convergence point from the binary image; and a calculation unit that acquires the distance L [mm] and the Vee convergence angle $\theta[°]$ based on the first Vee convergence point detected at the first detecting unit and the second Vee convergence point detected at the second detecting unit; and a determining unit that determines whether or not the distance L [mm] and the Vee convergence angle $\theta[°]$ measured by the measuring unit satisfy the following equation (1):

$$L_{min}(\theta/\theta_{st})^{-0.15} \leq L \leq 35 \qquad (1)$$

$L_{min}$ [mm]: Reference distance that is set in advance
$\theta_{st}[°]$: Reference angle that is set in advance.

2. The operation management device for high-frequency resistance welding and induction welding according to claim 1, the device further comprising, a control unit that controls an amount of heat input in such a manner that the distance L [mm] and the Vee convergence angle $\theta[°]$ that are measured by the measuring unit satisfy the equation (1).

* * * * *